United States Patent [19]

Guigan

[11] 4,244,916

[45] * Jan. 13, 1981

[54] DEVICE FOR CONDITIONING A SAMPLE OF LIQUID FOR ANALYZING WITH INTERNAL FILTER

[76] Inventor: Jean Guigan, 8, rue Jean Mermoz, 75008 Paris, France

[*] Notice: The portion of the term of this patent subsequent to May 15, 1996, has been disclaimed.

[21] Appl. No.: 9,718

[22] Filed: Feb. 5, 1979

Related U.S. Application Data

[63] Continuation-in-part of Ser. No. 837,055, Sep. 28, 1977, Pat. No. 4,154,793.

[30] Foreign Application Priority Data

Aug. 18, 1977 [FR] France .................................. 7725225
Apr. 28, 1978 [FR] France ................................ 78 12635

[51] Int. Cl.³ .................... G01N 21/07; G01N 31/00; C12M 1/12; C02F 1/38
[52] U.S. Cl. .................................... 422/72; 210/378; 210/927; 356/246; 356/427; 422/55; 422/57; 422/101; 435/311; 435/312; 210/380.1
[58] Field of Search ................... 356/246, 427; 422/55, 422/57, 58, 72, 101; 210/DIG. 23, 378, 380 R, 381; 435/311, 312

[56] References Cited

U.S. PATENT DOCUMENTS

| | | | |
|---|---|---|---|
| 1,793,204 | 2/1931 | Altpeter | 210/380 R |
| 3,568,838 | 3/1971 | Appelgren et al. | 210/380 R X |
| 3,733,179 | 5/1973 | Guehler | 422/72 X |
| 3,801,280 | 4/1974 | Shah et al. | 422/101 X |
| 3,882,716 | 5/1975 | Beiman | 422/72 X |
| 3,953,172 | 4/1976 | Shapiro et al. | 422/72 X |
| 4,083,784 | 4/1978 | Gine, Jr. | 210/DIG. 23 X |
| 4,154,793 | 5/1979 | Guigan | 422/72 X |

*Primary Examiner*—Joseph Scovronek
*Attorney, Agent, or Firm*—Sughrue, Rothwell, Mion, Zinn and Macpeak

[57] ABSTRACT

The device for conditioning a sample of liquid for medical analysis which comprises a plurality of calibrated peripheral cells connected to a central receptacle by way of ducts including an air inlet orifice for conveying the sample from the receptacle to the cell and to completely fill the cell by centrifugal action and employing an air escape orifice in each cell within a wall closer to the axis of rotation than that wall bearing the inlet orifice, carries a filter disposed between the central receptacle and the calibrated peripheral cell for prevention of solid particles in suspension from passing with the sample liquid from the central receptacle to the calibrated peripheral cells.

6 Claims, 4 Drawing Figures

DEVICE FOR CONDITIONING A SAMPLE OF LIQUID FOR ANALYZING WITH INTERNAL FILTER

This application is a continuation-in-part application of U.S. application Ser. No. 837,055 filed Sept. 28, 1977, to the applicant, and assigned to the common assignee and entitled "DEVICE FOR CONDITIONING A SAMPLE OF LIQUID FOR ANALYSING" now U.S. Pat. No. 4,154,793, issued May 15, 1979.

FIELD OF THE INVENTION

This invention relates to the conditioning of a sample of liquid for analysis. The conditioning takes place in a device which comprises a plurality of calibrated peripheral cells each having two parallel surfaces for optical measurement of the liquid and connected to a central receptacle for receiving the sample, each of the cells being intended for containing a reagent.

The device comprises for each cell, means for conveying the sample from the receptacle to the cell with a view to filling it completely by centrifuging and escape means for the air contained in the cell to the receptacle, the conveying means comprising an inlet orifice in each cell, the escape means comprising an orifice and leading into the receptacle, the orifices being of such a size as to retain the liquid contained in each cell after complete filling thereof.

The device preferably has at least one of the following characteristics.

The means for conveying the sample are constituted for each cell by at least one duct provided in a radial partition which delimits the cell, the duct connecting the central receptacle to the inlet orifice in the vicinity of which it has a constriction which prevents any return of liquid, the inlet orifice leading from the radial partition preferably into the vicinity of the surface of the furthest cell from the axis of rotation.

The duct is substantially L-shaped and has a long radial path.

The duct is substantially T-shaped so as to feed two neighboring cells and has a long radial path.

The duct is delimited by a groove formed in the upper wall of the associated radial partition and by the lower wall of a lid which closes the cells.

The duct is delimited by the upper surface of the associated radial partition and a groove formed in the lower wall of a lid which closes the cells.

Air escape means are constituted for each cell by a simple orifice formed in the wall of the nearest cell to the axis of rotation and whose cross-section, when there is no centrifuging, stops by capillarity the liquid which occupies the cell, the orifice being advantageously formed in the upper zone of the wall.

For each cell, the height of the nearest wall to the axis of rotation is greater than the height of the furthest wall from that axis, with a view to better expulsion of the air contained in the cell.

The central receptacle is delimited by a bottom with a raised peripheral edge and the central part of a lid for closing the cells in which is formed an opening for the sample to be inserted, the central part of the lid preferably being substantially dome shaped, the insertion being formed at the top of the dome.

The bottom of the receptacle has a central zone which is curved with a view to improved centrifuging of the sample.

The bottom of the receptacle has a few radial ribs which draw away the liquid during centrifuging.

The present invention aims to improve the previous device so that it can analyze liquids which contain solid particles in suspension. These liquids are, for example, blood, waste water, etc.

SUMMARY OF THE INVENTION

The present invention provides a device embodying the parent application, intended to analyze a sample of liquid which contains solid particles in suspension and comprising between the central receptacle and the calibrated peripheral cells, a filter capable of retaining the solid particles during centrifuging.

By way of example, the filter is a filtering gel, a cellulosic ester or asbestos.

According to a preferred embodiment, the filter is in the form of a cylindrical cartridge defining the lateral walls of the central receptacle.

In another embodiment of the invention, the filter is disposed in ducts connecting the central receptacle to the inlet orifices associated with the peripheral cells.

Other characteristics and advantages of the invention will become more clearly apparent from the following description, given by way of illustration but having no limiting character with reference to the figures of the accompanying drawings.

BRIEF DESCRIPTION OF THE DRAWINGS

Like elements bear like numerals in the various embodiments.

DESCRIPTION OF THE PREFERRED EMBODIMENTS

Figure 1:
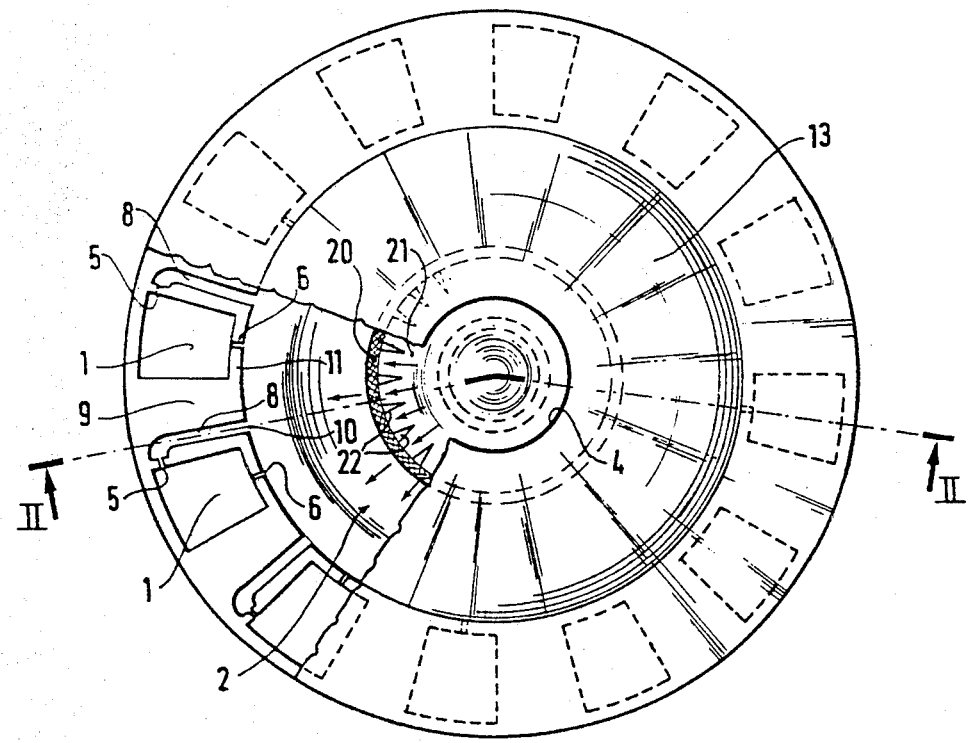
FIG. 1 is a top view of a conditioning device embodying the invention and whose lid has been partially cut away.
Figure 2:
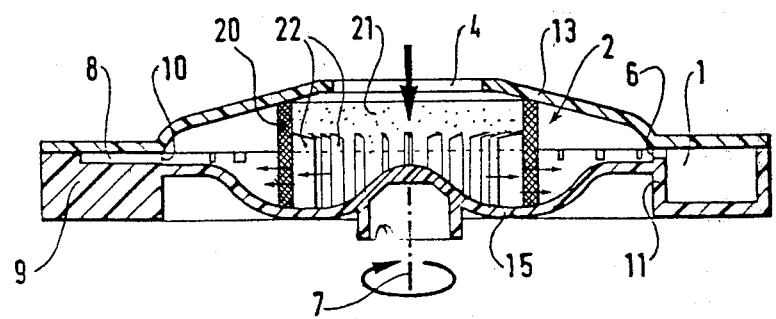
FIG. 2 is a cross-section along line II-II of FIG. 1.
Figure 3:
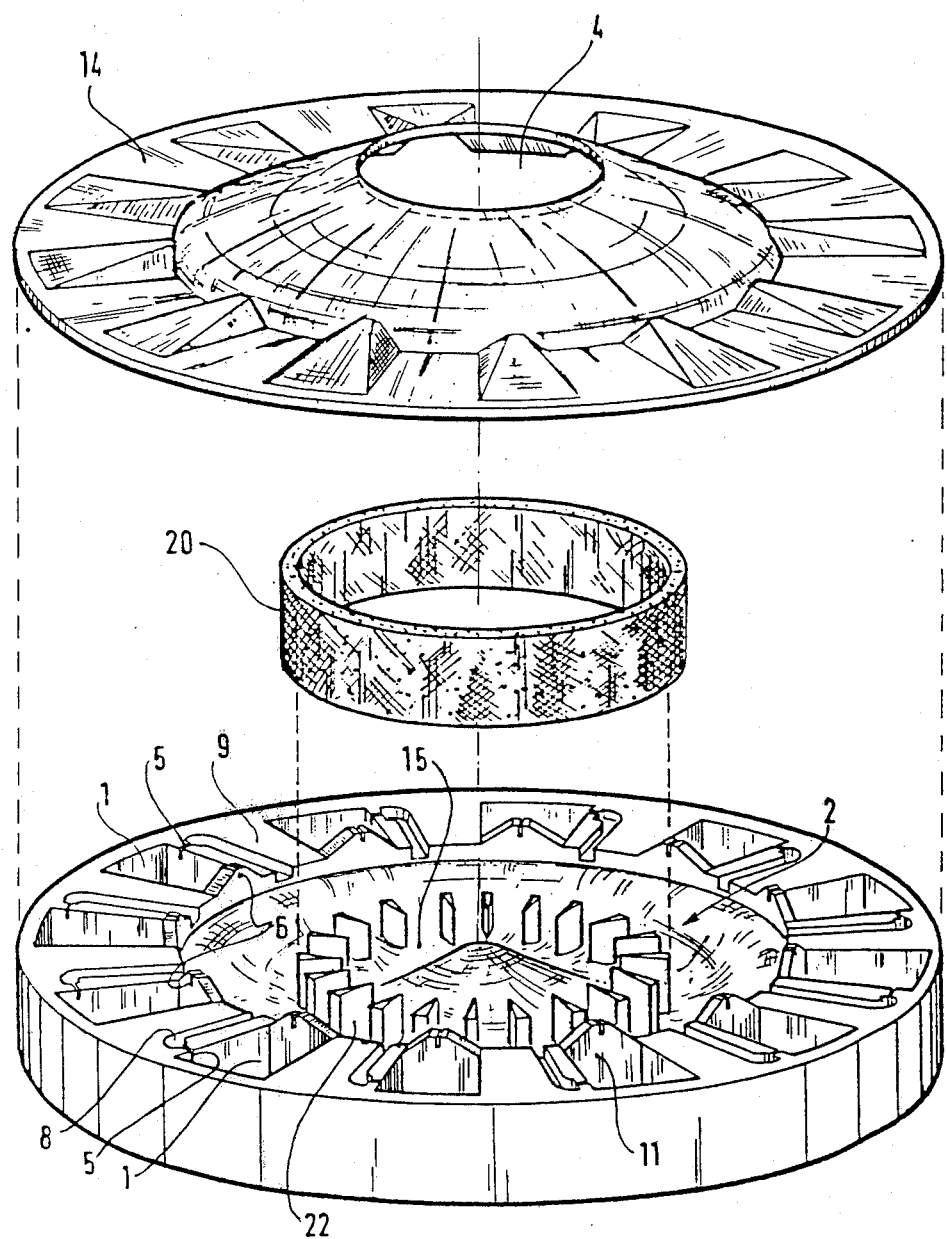
FIG. 3 is an exploded perspective view, partially cut away, of the device in another embodiment of the invention.

The device in both illustrated embodiments has symmetry of revolution about an axis 7. It is constituted by a plastics housing delimited by a bottom 15 and a lid (13 or 14 corresponding respectively to the variants of FIG. 1 and of FIG. 3. Internally, the housing includes a plurality of calibrated peripheral cells 1 each containing a reagent (not shown) deposited, for example, in the form of a lyophilized film. It also includes a compartment 2 divided by a filter 20 in cartridge form defining with the bottom 15 and the lids 13 and 14 a central receptacle 21 for the liquid to be analyzed. This liquid contains a solid substance in suspension. The porosity of the material of the filter 20 is chosen so as to stop the solid substance during centrifuging around the axis 7. Radial ribs 22 integral with the bottom 15 are provided inside the cartridge filter 20 so as to draw off the liquid during centrifuging.

As in the device of the parent application, the device includes means for conveying the filtered liquid from the receptacle 2 to each cell and air escape means to enable the air contained in each cell to escape to the compartment 2. The conveying means are constituted for each cell by at least one duct 8 formed in a radial partition 9 which delimits the cell, the duct connecting the central receptacle 2 by an input orifice 10 to the cell through the inlet orifice 5 in the vicinity of which it has a contriction which prevents any return of liquid. The air escape means are constituted by a simple orifice 6 formed in the wall 11 of the nearest cell to the axis of rotation and whose cross-section, when there is no centrifuging, stops by capillarity the liquid which occupies the cell.

The sample of liquid to be analyzed is inserted through a central opening 4 in the cover 13 or 14. It is rapidly centrifuged and guided in particular by ribs 22, against the cartridge filter 20 which filters it. Since centrifuging is continued, the filtered liquid is pushed strongly against the orifices 6 and 10. As stated in the main patent, the portion of the liquid which passes through the orifice 10 is canalized by the duct 8 up to the capillary end of the latter and to the inlet orifice 5. The input pressure at 5 is constantly greater than the input pressure at 6 because of the centrifugal force and because of its being further from the axis of rotation, so that the air contained in the cell is pushed by the liquid and escapes at 6. Filling continues until the air has completely escaped and balances the pressure on either side of the wall 11, as there is provided a sufficient quantity of sample for a portion thereof to be applied permanently against the wall 11, even when the cell is completely filled. During the whole filling and until the end of filling, any portion of liquid which has entered a cell cannot leave it because of the centrifugal force and when centrifuging ceases, the liquid which completely occupies the cell is retained between the orifices 5, 6 which thus form genuine gauge points defining a calibrated volume.

Figure 4:
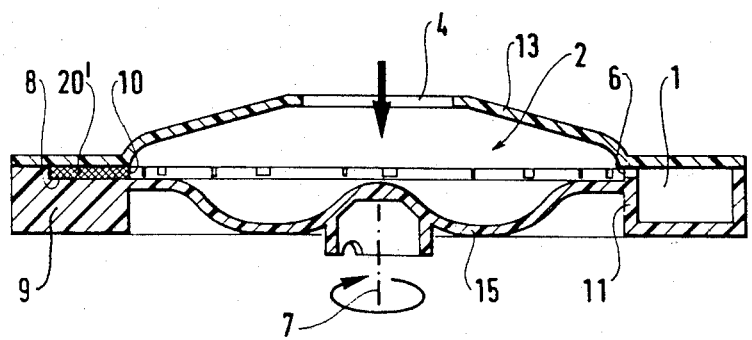
FIG. 4 is a vertical cross-section of an alternate embodiment of the present invention.

Reference to the vertical sectional view of FIG. 4 of an alternate embodiment in which common elements bear common numerical designation, the filter 20' in this case is not in the form of a cylindrical cartridge. In this case, the filter which may constitute a filtering gel, cellulosic ester or asbestos, fills the radial portion of duct 8. Alternatively, it may lie within duct 8 but extend only along a portion of that duct or comprise an annular element overlying the inlet orifices 10 at the entry end of duct 8.

While the invention has been particularly shown and described with reference to preferred embodiments thereof, it will be understood by those skilled in the art that the foregoing and other changes in form and details may be made therein without departing from the spirit and scope of the invention.

I claim:

1. In a device for conditioning a sample of liquid for analyzation, said device comprising:
   a central receptacle,
   a plurality of calibrated peripheral cells on the periphery of the central receptacle, each cell having two parallel walls for an optical measurement and connected to said central receptacle receiving said sample, each of said cells being a reagent containing cell,
   said device further comprising for each cell, means for conveying the sample of liquid from the receptacle to said cell to fill it completely by centrifuging and escape means for the air contained in said cell to said receptacle,
   said conveying means comprising an inlet orifice in each cell,
   said escape means comprising an orifice nearer to the axis of rotation than said inlet orifice and leading into said receptacle,
   said orifices being of such size as to retain the liquid contained in each cell after complete filling thereof, and centrifuging has ceasesd,
   the improvement comprising a filter disposed between the central receptacle and said calibrated peripheral cells for prevention of passage of solid particles in suspension from said central receptacle to said calibrated peripheral cells.

2. The device according to claim 1, wherein said filter comprises a cylindrical cartridge forming a lateral wall of said central receptacle.

3. The device according to claim 1, wherein said filter is carried by said conveying means.

4. The device according to claim 1, wherein said filter comprises a material chosen from the group consisting of a filtering gel, cellulosic ester and asbestos.

5. The device according to claim 1, wherein each cell is delimited by a radial partition, said means for conveying said sample comprises at least one duct formed in said radial partition, said duct connecting the central receptacle to the inlet orifice, and a construction is provided within said duct in the vicinity of said inlet orifice for preventing any return of liquid, and wherein said filter is disposed within said duct upstream of said inlet orifice.

6. The device according to claim 5, wherein said filter comprises a material from the group consisting of a filtering gel, cellulosic ester and asbestos.

* * * * *